United States Patent
Nishi et al.

(10) Patent No.: US 11,812,935 B2
(45) Date of Patent: Nov. 14, 2023

(54) ENDOSCOPE CLEANING WORK SUPPORT DEVICE, METHOD OF OPERATING ENDOSCOPE CLEANING WORK SUPPORT DEVICE, AND ENDOSCOPE CLEANING WORK SUPPORT PROGRAM

(71) Applicant: OLYMPUS CORPORATION, Tokyo (JP)

(72) Inventors: Tetsuya Nishi, Tokyo (JP); Hikari Shimizu, Tokyo (JP); Clarinda Kuan, Tokyo (JP); Kaori Kitano, Tokyo (JP); Yoshiko Ikeda, Tokyo (JP); Takeshi Nishiyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 562 days.

(21) Appl. No.: 16/861,426

(22) Filed: Apr. 29, 2020

(65) Prior Publication Data
US 2020/0260943 A1    Aug. 20, 2020

Related U.S. Application Data

(63) Continuation of application No. PCT/JP2018/034453, filed on Sep. 18, 2018.

(30) Foreign Application Priority Data

Oct. 31, 2017 (JP) ................. 2017-211131

(51) Int. Cl.
*A61B 1/12* (2006.01)
*B08B 9/04* (2006.01)
(Continued)

(52) U.S. Cl.
CPC ............... *A61B 1/121* (2013.01); *B08B 9/04* (2013.01); *G06F 3/14* (2013.01); *A61B 1/00009* (2013.01)

(58) Field of Classification Search
CPC ... A61B 1/121; A61B 2090/702; A61B 90/70; G06F 3/14; G06F 3/048
See application file for complete search history.

(56) References Cited

U.S. PATENT DOCUMENTS

2008/0099045 A1*   5/2008   Glenn .................. G08B 21/245
                                                                134/18

FOREIGN PATENT DOCUMENTS

JP        2007-325724 A      12/2007
JP        2010-035850 A       2/2010
(Continued)

OTHER PUBLICATIONS

Machine translation: Yazawa et al.; JP2017000441 (Year: 2017).*
(Continued)

*Primary Examiner* — Natasha N Campbell
(74) *Attorney, Agent, or Firm* — Scully, Scott, Murphy & Presser, P.C.

(57) ABSTRACT

In an endoscope cleaning work support device, an operation reception unit received an input from a cleaner. A display control unit controls the display unit to display a procedure for manual cleaning of an endoscope on a display unit step by step. A measurement unit measures a first period of time from a start time of a procedure in a current step marked by reception of an input for displaying the procedure in the current step by the operation reception unit, to an end time of the procedure in the current step marked by reception of an input for displaying a procedure in a subsequent step by the operation reception unit. A comparison determination unit compares a reference period of time defined for each step for displaying the procedure with the first period of time. The display control unit displays information for alerting the cleaner when the first period of time is shorter than the reference period of time on the display unit.

20 Claims, 10 Drawing Sheets

(51) Int. Cl.
G06F 3/14 (2006.01)
A61B 1/00 (2006.01)

(56) References Cited

FOREIGN PATENT DOCUMENTS

| | | |
|---|---|---|
| JP | 2010-200993 A | 9/2010 |
| JP | 2014-057753 A | 4/2014 |
| JP | 2017-000441 A | 1/2017 |
| JP | 2017-131335 A | 8/2017 |

OTHER PUBLICATIONS

Machine translation: Matsushima, D.; JP2017131335 (Year: 2017).*
International Search Report dated Nov. 6, 2018 issued in International Application No. PCT/JP2018/034453.
International Preliminary Report on Patentability dated May 5, 2020 together with the Written Opinion from related International Application No. PCT/JP2018/034453.

* cited by examiner

FIG. 4A

| SKILL LEVEL TABLE | | | |
|---|---|---|---|
| CLEANER | ENDOSCOPE MODEL A | ENDOSCOPE MODEL B | ENDOSCOPE MODEL C |
| CLEANER X ID:N0001 | SKILL LEVEL:1 | SKILL LEVEL:2 | SKILL LEVEL:3 |
| CLEANER Y ID:N0002 | SKILL LEVEL:3 | SKILL LEVEL:1 | SKILL LEVEL:2 |
| CLEANER Z ID:N0003 | SKILL LEVEL:2 | SKILL LEVEL:3 | SKILL LEVEL:1 |

FIG. 4B

| SKILL LEVEL/CONTENT ASSOCIATION TABLE | | | |
|---|---|---|---|
| SKILL LEVEL | ENDOSCOPE MODEL A | ENDOSCOPE MODEL B | ENDOSCOPE MODEL C |
| 1 | CONTENT:A1 | CONTENT:B1 | CONTENT:C1 |
| 2 | CONTENT:A2 | CONTENT:B2 | CONTENT:C2 |
| 3 | CONTENT:A3 | CONTENT:B3 | CONTENT:C3 |

ENDOSCOPE CLEANING WORK SUPPORT DEVICE, METHOD OF OPERATING ENDOSCOPE CLEANING WORK SUPPORT DEVICE, AND ENDOSCOPE CLEANING WORK SUPPORT PROGRAM

CROSS-REFERENCE TO RELATED APPLICATIONS

This application is based upon and claims the benefit of priority from International Application No. PCT/JP2018/034453, filed on Sep. 18, 2018, the entire contents of which are incorporated herein by reference.

BACKGROUND OF THE INVENTION

1. Field of the Invention

The present invention relates to an endoscope cleaning work support device for supporting the manual cleaning of an endoscope by a cleaning worker, a method of operating the endoscope cleaning work support device, and an endoscope cleaning work support program.

2. Description of the Related Art

In medical facilities, endoscopes used in examinations are cleaned and disinfected after the examinations in order to be used for the next examination. If the cleaning and disinfection are not sufficient, infection may be caused. On the other hand, a system has been suggested that allows a cleaner to easily check a work procedure by displaying a standardized work procedure of a cleaning process on a screen of a predetermined terminal device.

Even when the work procedure of a cleaning process is displayed on a screen as described above, the quality of the cleaning may vary depending on the cleaner. This tendency occurs especially in manual cleaning. For example, in a specific step of the manual cleaning, some cleaners complete work of the step without taking necessary time.

SUMMARY OF THE INVENTION

In this background, a purpose of the present invention is to provide a technique for supporting the uniformization of the cleaning quality in manual cleaning of endoscopes.

An endoscope cleaning work support device according to one embodiment of the present invention includes: an operation reception unit that receives an input from a cleaner; a display control unit that performs control so as to display a procedure for manual cleaning of an endoscope on a display unit step by step; a first measurement unit that measures a first period of time from a start time of a procedure in a current step marked by reception of an input for displaying the procedure in the current step by the operation reception unit, to an end time of the procedure in the current step marked by reception of an input for displaying a procedure in a subsequent step by the operation reception unit; and a comparison unit that compares a reference period of time defined for each step for displaying the procedure with the first period of time. The display control unit displays information for alerting the cleaner when the first period of time is shorter than the reference period of time.

Another embodiment of the present invention relates to a method of operating an endoscope cleaning work support device. This method includes: allowing an operation reception unit to receive an input from a cleaner by; allowing the display control unit to perform control so as to display a procedure for manual cleaning of an endoscope on a display unit step by step; allowing the measurement unit to measure a first period of time from a start time of a procedure in a current step marked by reception of an input for displaying the procedure in the current step by the operation reception unit, to an end time of the procedure in the current step marked by reception of an input for displaying a procedure in a subsequent step; allowing the comparison unit to compare a reference period of time defined for each step for displaying the procedure with the first period of time; and allowing the display control unit to display information for alerting the cleaner when the first period of time is shorter than the reference period of time.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIGS. 4A and 4B are diagrams respectively showing an example of a skill level table constructed in a skill level information storage and an example of a skill level/content association table constructed in a skill level/content association information storage;

DETAILED DESCRIPTION OF THE INVENTION

The invention will now be described by reference to the preferred embodiments. This does not intend to limit the scope of the present invention, but to exemplify the invention.

At a medical facility, after an endoscopic examination is completed, an endoscope used for the examination is cleaned and disinfected. The reprocess step of the endoscope after the completion of the examination proceeds as follows. First, a medical professional such as a nurse or technician who is in charge of cleaning (hereinafter referred to as a "cleaner") wipes the used endoscope placed in the examination room with gauze or a cloth to sufficiently remove mucus, blood, and dirt and then transports the endoscope to a cleaning room. A cleaning table (sink) and a cleaning device are installed in the cleaning room. In the cleaning room, the cleaner first manually cleans the endoscope. Next, the endoscope that has been manually-cleaned is installed in the cleaning device, and the endoscope is mechanically cleaned. Lastly, the cleaned endoscope is stored in a storage. Among these steps, the present embodiment focuses on a manual cleaning step.

Figure 1:
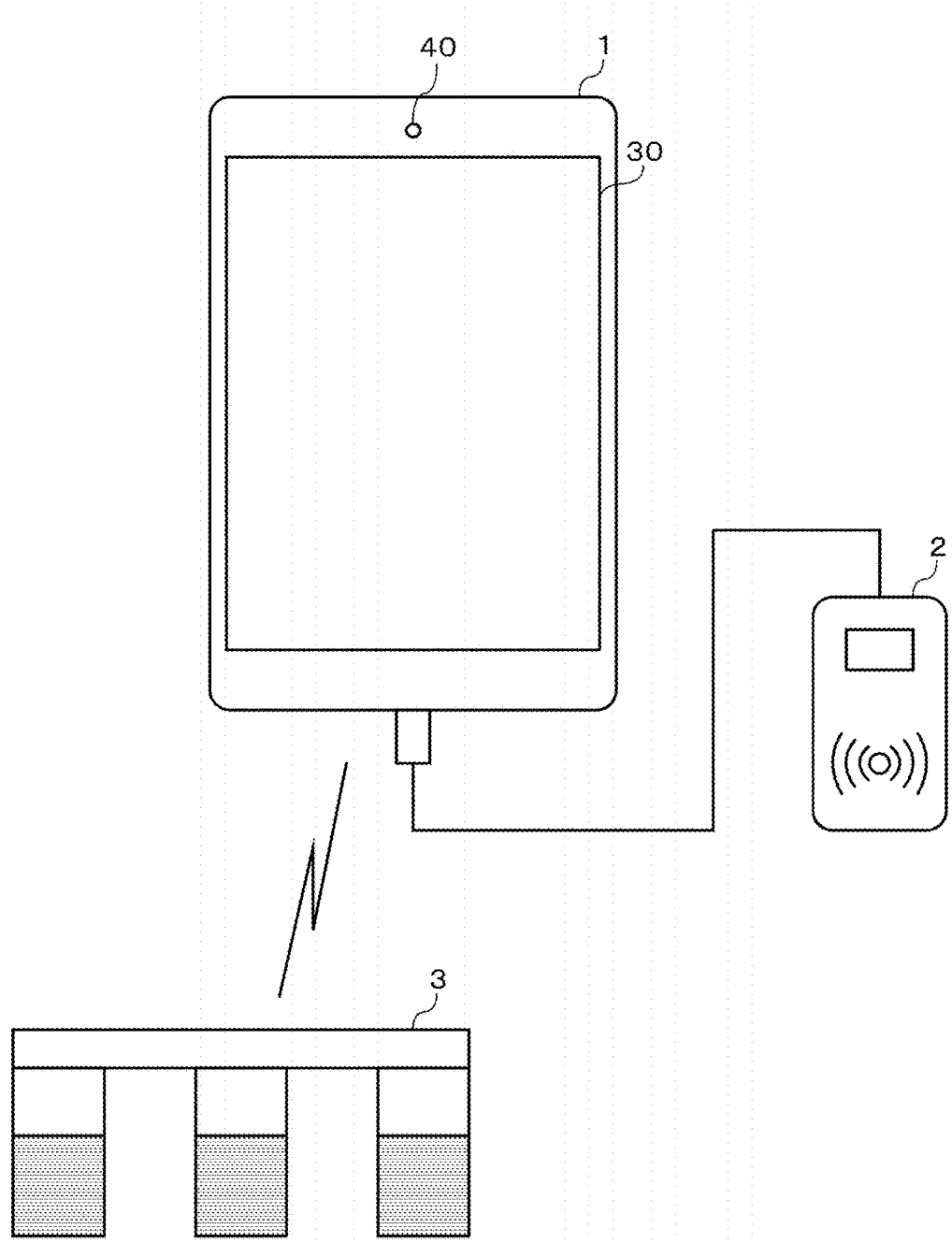
FIG. 1 is a diagram illustrating a schematic configuration of an endoscope cleaning work support device according to an embodiment of the present invention.

FIG. 1 is a diagram illustrating a schematic configuration of an endoscope cleaning work support device 1 according to an embodiment of the present invention. As shown in FIG. 1, in the present embodiment, an example will be described in which the endoscope cleaning work support device 1 is formed of a tablet terminal device. The endoscope cleaning work support device 1 is installed near a cleaning table (sink) for manually cleaning an endoscope. More specifically, the endoscope cleaning work support device 1 is installed at a position and in a direction that allow a touch panel display 30 to be in the field of view of the cleaner when the cleaner manually cleans the endoscope.

The endoscope cleaning work support device 1 is connected to a tag reader 2. The endoscope cleaning work support device 1 and the tag reader 2 may be connected by, for example, a wire such as a Lightning (registered trademark) cable or a USB cable, or may be connected wirelessly by Bluetooth (registered trademark), Wi-Fi (registered trademark), or the like. FIG. 1 illustrates an example of a wired connection.

A tag such as a radio frequency identifier (RFID) or the like is attached to each endoscope. Further, each cleaner holds an ID card equipped with a tag such as an RFID. The cleaner holds the tag of the endoscope over the tag reader 2 before starting the cleaning of the endoscope. The tag reader 2 reads endoscope information including the model of the endoscope from the tag of the endoscope that is held over the tag reader 2 and transmits the endoscope information that is read to the endoscope cleaning work support device 1.

The cleaner holds his/her ID card over the tag reader 2 before starting the cleaning of the endoscope. The tag reader 2 reads cleaner information including the identification information of the cleaner from the tag of the ID card that is held over the tag reader 2 and transmits the cleaner information that is read to the endoscope cleaning work support device 1.

Some endoscope cleaning work support devices 1 have a tag reading function built into the main unit thereof. In this case, the external tag reader 2 is unnecessary, and the cleaner holds the tag of the endoscope and the tag of the ID card over the main unit of the endoscope cleaning work support device 1.

In general, the operation of a tablet terminal device is performed by touching a touch panel display with a finger. However, during the manual cleaning of the endoscope, the hands of the cleaner are basically full. Even if the manual cleaning is suspended temporarily, the hands are wet. Therefore, it is desirable to provide a user interface other than the touch panel display 30. FIG. 1 illustrates an example in which a foot pedal is used as an operation input device 3 other than the touch panel display 30.

The foot pedal includes at least one pedal, and each pedal is associated with a specific operation. For example, operations such as "forward", "go back one", "return to home", and "enter" are associated with respective pedals. The cleaner can perform a desired operation by stepping on the corresponding pedal.

A headset may be used as the operation input device 3 instead of the foot pedal. In that case, the cleaner can perform a desired operation through voice input. Although input accuracy decreases compared to when a headset is used, voice input may be performed using a microphone built in the main unit of the endoscope cleaning work support device 1.

The endoscope cleaning work support device 1 and the operation input device 3 may be connected by, for example, a wire such as a Lightning (registered trademark) cable or a USB cable, or may be connected wirelessly by Bluetooth (registered trademark), Wi-Fi (registered trademark), or the like. FIG. 1 illustrates an example where the foot pedal is wirelessly connected.

Figure 2:
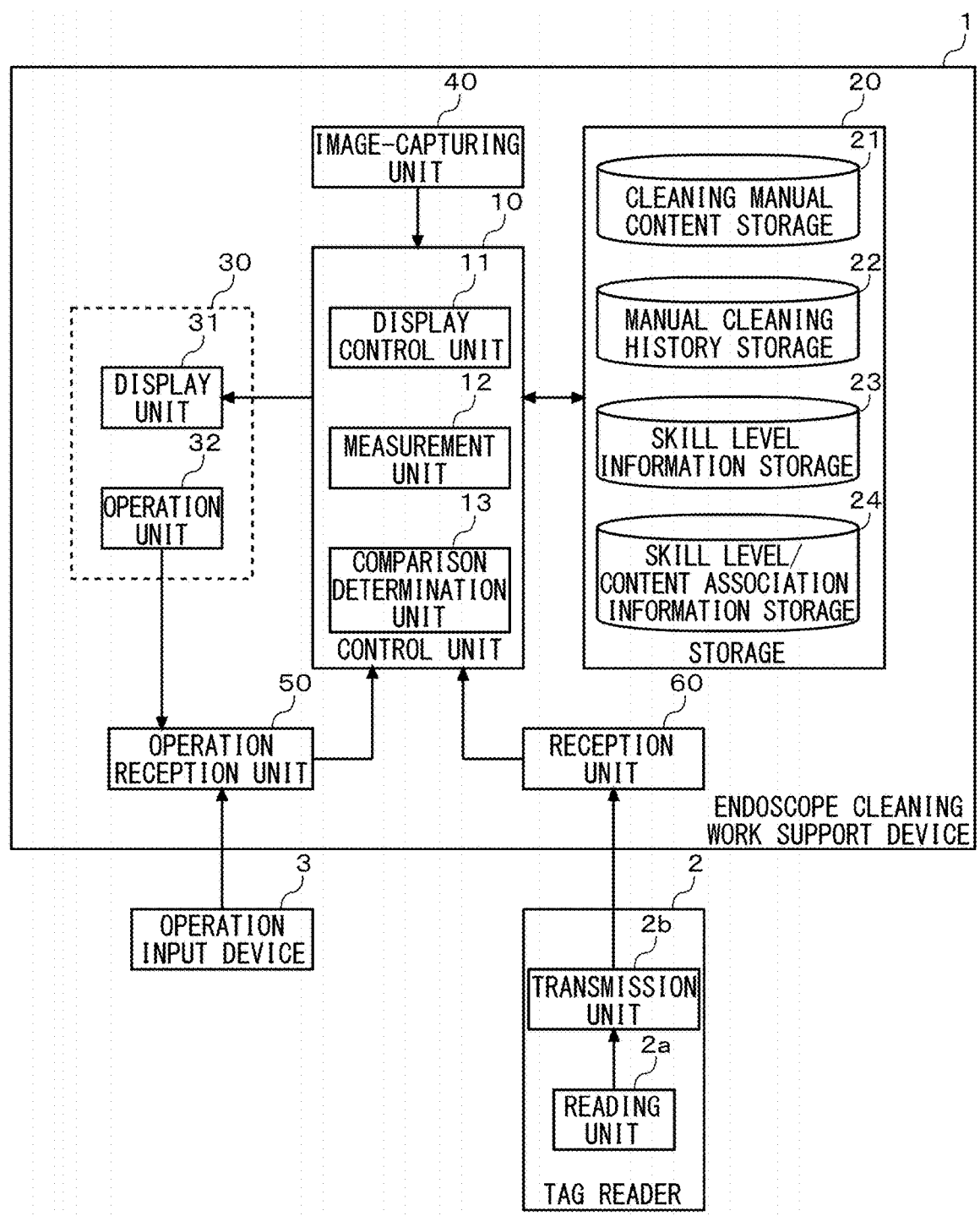
FIG. 2 is a diagram illustrating functional blocks of the endoscope cleaning work support device according to the embodiment of the present invention.

FIG. 2 is a diagram illustrating functional blocks of the endoscope cleaning work support device 1 according to the embodiment of the present invention. The endoscope cleaning work support device 1 includes a control unit 10, a storage 20, a display unit 31, an operation unit 32, an image-capturing unit 40, an operation reception unit 50, and a reception unit 60.

The display unit 31 includes a liquid crystal display or an organic EL display and displays an image signal supplied from the control unit 10 on a screen. The operation unit 32 includes a touch panel and/or a physical button, converts a physical operation from a user into an electric operation signal, and outputs the electric operation signal to the operation reception unit 50. The operation reception unit 50 is an I/O interface that receives an operation signal that is input from the operation unit 32 or the operation input device 3 and outputs the received operation signal to the control unit 10.

The reception unit 60 is a reception unit for short-range wireless communication (for example, Bluetooth (registered trademark), Wi-Fi (registered trademark), infrared communication). In FIG. 2, a wireless signal transmitted from a transmission unit 2b of the tag reader 2 is received. The tag reader 2 includes a reading unit 2a and the transmission unit 2b. The reading unit 2a reads endoscope information/cleaner information from a tag held over by the cleaner. The transmission unit 2b transmits the endoscope information/cleaner information that is read by the reading unit 2a to the reception unit 60 using short-range wireless communication. The reception unit 60 outputs the received endoscope information/cleaner information to the control unit 10.

The image-capturing unit 40 is an image-capturing unit installed on the front surface (the surface on which the touch panel display 30 is installed) of the housing of the endoscope cleaning work support device 1. The image-capturing unit 40 is basically an image-capturing unit for capturing images of the user of the endoscope cleaning work support device 1. The image-capturing unit 40 is provided with a solid-state imaging device (for example, CCD image sensor or CMOS image sensor) and a signal processing circuit. The solid-state imaging device converts incident light into an electrical signal. The signal processing circuit performs signal processing such as A/D conversion, noise removal, and the like on an image signal generated by photoelectric-conversion by the solid-state imaging device and outputs the image signal to the control unit 10.

The storage 20 includes a cleaning manual content storage 21, a manual cleaning history storage 22, a skill level information storage 23, and a skill level/content association information storage 24. The storage 20 is comprised of a nonvolatile memory (for example, a NAND-type flash memory).

The cleaning manual content storage 21 holds cleaning manual content for each endoscope model. The cleaning manual content is content that shows a procedure of manual cleaning of the endoscope by a cleaner using a still image/moving image for each step. All the steps of the manual cleaning may be shown by a still image or may be shown by a moving image. Also, only steps including complicated procedures may be shown by a moving image, and other steps may be shown by a still image. In each step, voice guidance may be added in addition to the still image/moving image.

Figure 3:
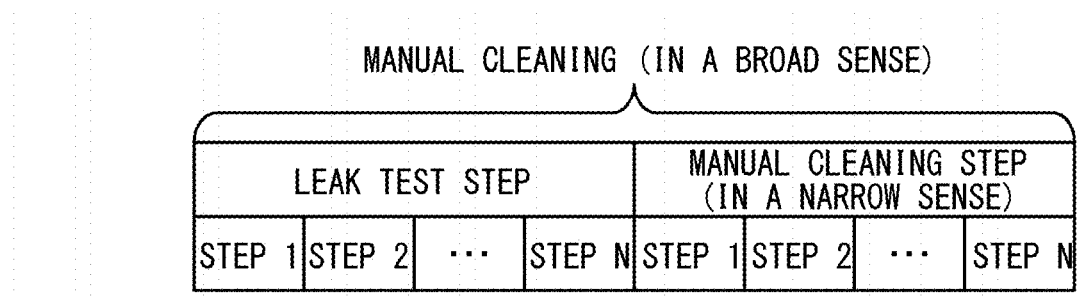
FIG. 3 is a diagram in which the steps of manual cleaning of an endoscope are classified.

FIG. 3 is a diagram in which the steps of manual cleaning of an endoscope are classified. The manual cleaning (in a broad sense) of an endoscope is classified into two major steps, a leak test step and a manual cleaning step (in a narrow sense). The leak test step is an examination step for checking whether or not a hole is formed in the endoscope. The manual cleaning step (in a narrow sense) is a step of actually cleaning the endoscope with the hands of a cleaner.

The leak test step and the manual cleaning step (in a narrow sense) each include a plurality of steps as minor steps. The number of the respective minor steps included in the leak test step and the manual cleaning step (in a narrow sense) varies depending on the type of endoscope. Basically, the higher the functionality of an endoscope becomes, the greater the number of the steps becomes. The manual cleaning step (in a narrow sense) includes a step of removing accessory parts (for example, an air/water feeding button, a suction button, a forceps plugs, etc.) from the endoscope so as to clean the accessory parts and a step of cleaning the inside of the channel with a brush. As described above, the number of steps in the manual cleaning step (in a narrow sense) varies depending on the number of accessory parts and the shape of the channel.

A plurality of types of cleaning manual content may be prepared for endoscopes of the same model according to the skill level of the cleaner. More specifically, the more detailed and attentive content is prepared as the skill level becomes low. For example, in cleaning manual content for beginners, a series of procedures is classified into more detailed steps, and each step is carefully explained with moving images and audio. In contrast, for example, in the cleaning manual content for advanced users, a series of procedures is classified into larger units of steps, and each step is indicated only by a still image.

FIGS. 4A and 4B are diagrams respectively showing an example of a skill level table 23a constructed in the skill level information storage 23 and an example of a skill level/content association table 24a constructed in the skill level/content association information storage 24. The skill level table 23a shown in FIG. 4A is a table that defines the skill level of cleaners for each endoscope model. For example, the skill level of each cleaner may be determined based on the accumulated cleaning time for each model or may be determined based on recognition by the supervisor.

The skill level/content association table 24a shown in FIG. 4B is a table that defines the relationship between the skill level and the content to be used for each endoscope model. The skill level/content association table 24a is unnecessary when a plurality of types of content are not prepared for each model.

FIG. 2 is referred back. The manual cleaning history storage 22 holds the cleaning history of each manual cleaning. The cleaning history includes at least the identification information of the endoscope, the model of the endoscope, the identification information of the cleaner, and the start time and the end time of the manual cleaning step (in a broad sense). Further, the working time for each minor step may be included.

The control unit 10 includes a display control unit 11, a measurement unit 12, and a comparison determination unit 13. The control unit 10 can be realized by the cooperation of hardware resources and software resources or only by hardware resources. As the hardware resources, processors, ROM, RAM, and other LSIs can be used. A CPU, a GPU, and the like can be used as the processors. Programs such as operating systems and applications can be used as the software resources.

The display control unit 11 controls the display unit 31 to display, for each step, still/moving image content indicating a procedure for manually cleaning the endoscope. The cleaner proceeds with the work of each step while looking at the still/moving image content displayed on the display unit 31. When the work of a single step is completed, the cleaner enters a step update instruction to the operation input device 3 or the touch panel display 30.

In each step, the measurement unit 12 measures the working time of each step by measuring the time during which the content indicating the procedure of the step is displayed. More specifically, the measurement unit 12 measures a period of time from a start time of the procedure in the current step marked by reception of an input for displaying the procedure in the current step by the operation reception unit 50, to an end time of the procedure in the current step. The end time of the procedure in the current step is determined being marked by reception of an update instruction input from a cleaner for switching the screen display to content indicating a procedure in the subsequent step by the operation reception unit 50. More specifically, as the start time of the procedure in the current step, the time at which the operation reception unit 50 receives an update instruction input may be used, or the time at which the display of the content indicating the procedure in the current step is started after the operation reception unit 50 receives the update instruction input may be used. Further, as the end time of the procedure in the current step, the time at which the operation reception unit 50 receives an update instruction input may be used, or the time at which the display of the content indicating the procedure in the current step is ended after the operation reception unit 50 receives the update instruction input may be used.

The comparison determination unit 13 compares a reference period of time defined for each step for displaying the procedure with a measured period of time measured by the measurement unit 12. When the measured period of time for the step is shorter than the reference period of time for the step, the comparison determination unit 13 determines that work of the current step has not been done sufficiently. The reference period of time for each step may be set by an endoscope maker or may be set by a medical institution where the endoscope is used. Further, a plurality of different reference periods of time may be set for each step according to the skill level of the cleaner. Further, the reference period of time for each step can be appropriately changed according to the change in the guideline or the actual situation.

When the measured period of time for the step is shorter than the reference period of time for the step, the display control unit 11 displays alert information for alerting the cleaner on the display unit 31. The alert information may be output using sound from a speaker (not shown) together with the display.

First Exemplary Embodiment

Figure 5:
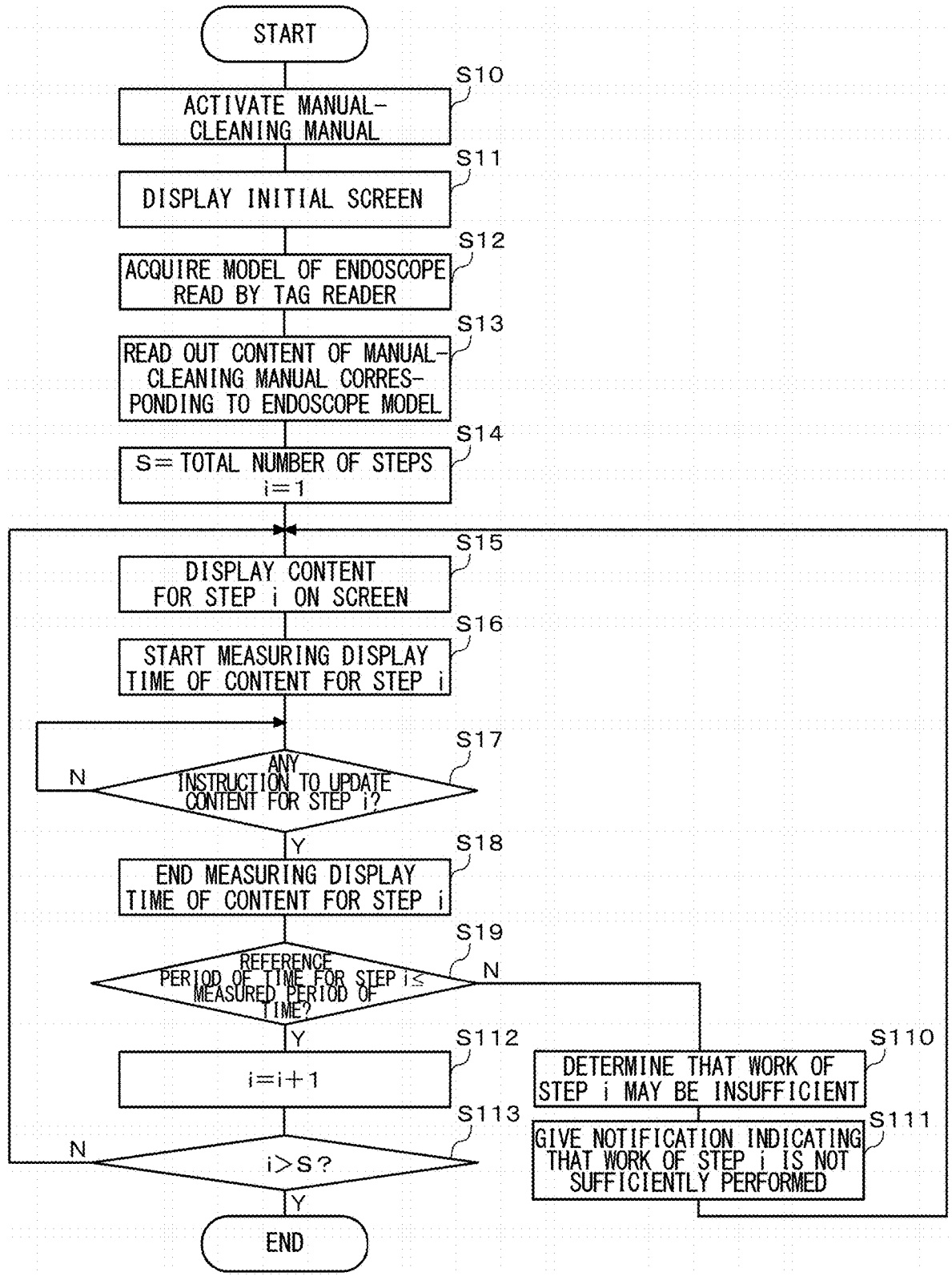
FIG. 5 is a flowchart illustrating a flow of a cleaning work support process according to the first exemplary embodiment.

FIG. 5 is a flowchart illustrating a flow of a cleaning work support process according to the first exemplary embodiment. The control unit 10 of the endoscope cleaning work support device 1 activates a manual-cleaning manual application (S10) and displays the initial screen of the manual-cleaning manual application on the display unit 31 (S11). The control unit 10 acquires the model of an endoscope included in endoscope information read by the tag reader 2 (S12). The control unit 10 reads out cleaning manual content corresponding to the acquired model of the endoscope from the cleaning manual content storage 21 (S13). The control unit 10 sets the total number of steps of the read cleaning manual content as a parameter S and sets 1 as the initial value for a parameter i (S14).

If cleaning manual content that differs according to the skill level is prepared, the following process is additionally performed. The control unit 10 acquires a cleaner ID included in cleaner information read by the tag reader 2. The control unit 10 acquires the skill level of the cleaner in reference to the skill level table 23a based on the acquired cleaner ID. In reference to the skill level/content association table 24a, the control unit 10 reads out cleaning manual content according to the model of the endoscope and the skill level of the cleaner.

The display control unit 11 causes the content for a step i of the read cleaning manual content to be displayed on the screen of the display unit 31 (S15). The measurement unit 12 starts measuring the display time of the content for the step i (S16). When an instruction to update the content in the step i is entered by the cleaner (Y in S17), the display control unit 11 ends the display of the content for the step i, and the measurement unit 12 ends the measurement of the display time of the content for the step (S18).

The comparison determination unit 13 compares the reference period of time for the step i with the measured period of time (S19). When the measured period of time is shorter than the reference period of time for the step i (N in S19), the comparison determination unit 13 determines that the work of the step i may be insufficient (S110). The display control unit 11 displays on the screen of the display unit 31 that the work of the step i is not sufficiently performed (S111). The step proceeds to step S15 so as to display the content for the step i from the beginning (S15).

When the measured period of time is equal to or longer than the reference period of time for the step i (Y in S19), the parameter i is incremented (S112). While the value of the parameter i is equal to or less than the value of the parameter S (N in S113), the step proceeds to step S15 so as to display content for the subsequent step i (S15). When the value of the parameter i exceeds the value of the parameter S (Y in S113), the work of all the steps in the manual cleaning step (in a broad sense) is ended. When the work of all the steps is completed, the control unit 10 records cleaning history information including the working time of each step in the manual cleaning history storage 22.

The comparison between the measured period of time and the reference period of time in the step S19 may be performed for each minor step or may be performed for each major step. For example, when the skill level is lower than a predetermined level, the comparison may be performed for each minor step, and when the skill level is higher than a predetermined level, the comparison may be performed for each major step.

Figure 6:
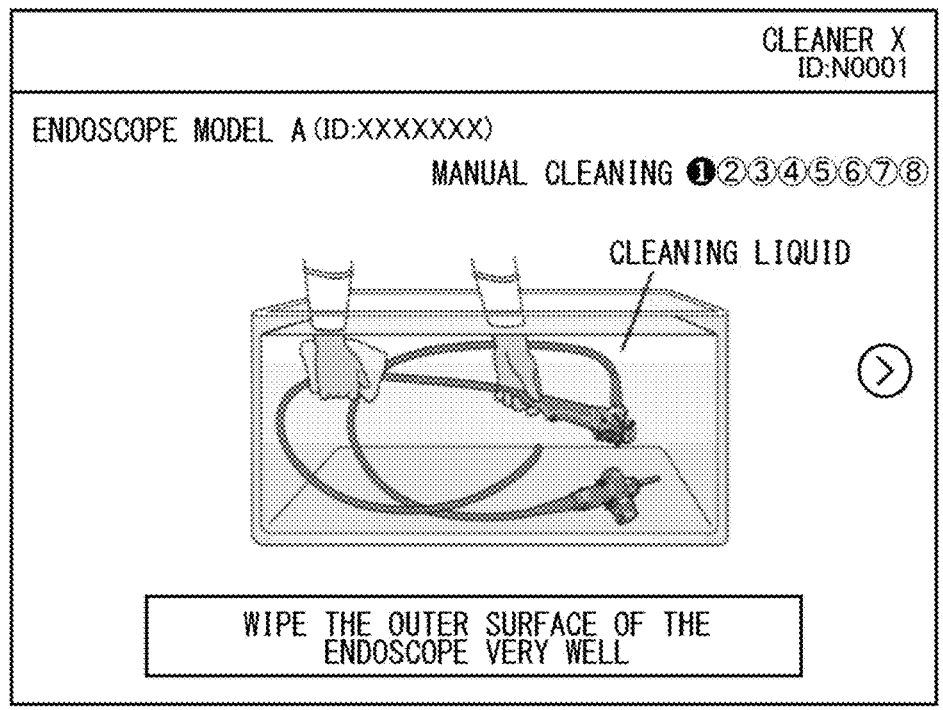
FIG. 6 is a diagram showing an example of content in the first step of a manual cleaning step (in a narrow sense)

FIG. 6 is a diagram showing an example of content in the first step of the manual cleaning step (in a narrow sense). The manual cleaning step (in a narrow sense) of an endoscope model A shown in FIG. 6 includes eight minor steps. FIG. 6 shows content in a step of immersing an endoscope in a cleaning liquid and wiping the outside of the endoscope with a sponge or gauze, which is the first step.

Figure 7:
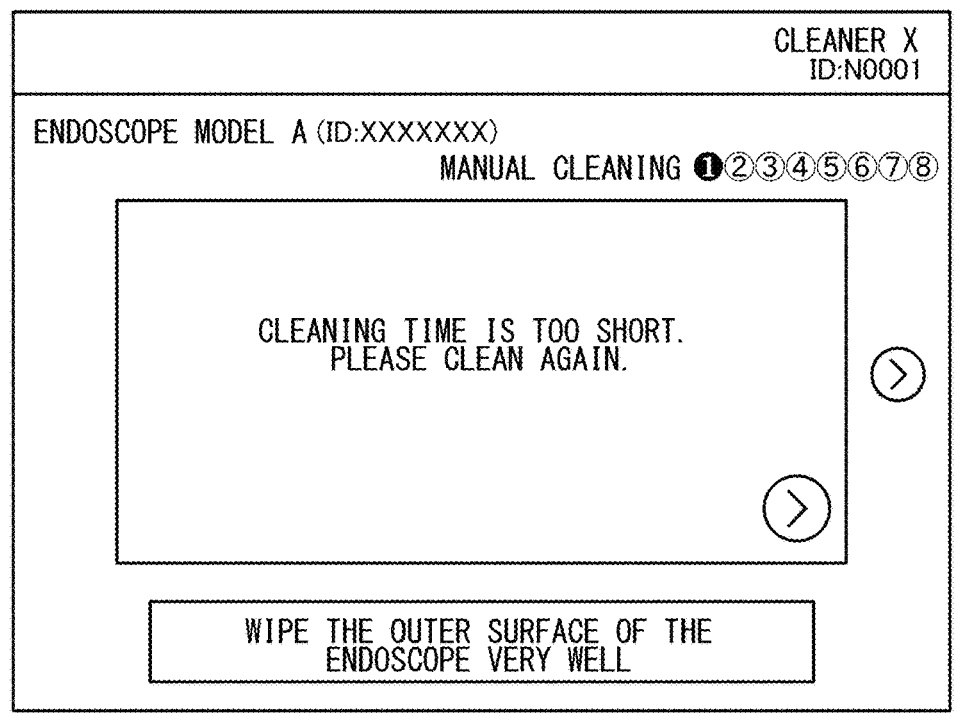
FIG. 7 is a diagram showing an example of an alert screen displayed when there is a possibility that the working time is insufficient.

FIG. 7 is a diagram showing an example of an alert screen displayed when there is a possibility that the working time is insufficient. FIG. 7 shows a screen that is displayed when the cleaner steps on a "forward" foot pedal before the reference period of time for the first step elapses while the content for the first step of the manual cleaning step (in a narrow sense) shown in FIG. 6 is displayed. By looking at this screen, the cleaner recognizes that the work of the first step may be insufficient. When a predetermined period elapses after the alert screen is displayed or when the cleaner steps on a "go back one" foot pedal, the content for the first step is displayed from the beginning, the measured period of time of the first step is reset, and the counting of a measured period of time is started again.

As described above, according to the first exemplary embodiment, in the manual cleaning step (in a broad sense) of an endoscope, the display control unit 11 displays alert information on a screen when a period of time measured by the measurement unit 12 is shorter than a reference period of time for displaying a procedure determined for each step. Thereby, the cleaner can be prompted to perform the cleaning for a necessary period of time. By looking at the screen, the cleaner can recognize that the work of the current step may be insufficient and can perform the work of the current step again. Further, since whether or not the work of each step is sufficient is determined based on time, it is possible to suppress a variation in the quality of cleaning performed by a cleaner.

Second Exemplary Embodiment

In the second exemplary embodiment, a case is considered where work that is interrupting emerges such as helping other staff temporarily suspending the cleaning work. When the cleaner is temporarily suspending the cleaning works, the cleaner enters an instruction to pause to the operation input device 3 or the operation unit 32. When the operation reception unit 50 receives an input instructing to pause, the display control unit 11 pauses the content displaying the procedure in the current step in a state where the content is rewound for a predetermined period of time, and the measurement unit 12 puts back the working time count of the current step by the predetermined period of time. For example, if the predetermined time is set to 5 seconds, and if an input to pause is entered at the time when 20 seconds have elapsed from the start of the work of the current step, the display control unit 11 changes the display of the content back to the display shown at the time when 15 seconds have elapsed, and the measurement unit 12 changes the working time count from 20 seconds to 15 seconds. As described, when an input to pause is entered, the display of the content and the working time count are put back by a predetermined time, thereby compensating for a time lag from the time when the work of the cleaner is actually stopped to the time when the worker enters the input to pause.

When the operation reception unit 50 receives an input instructing to pause, the display control unit 11 may pause the content displaying the procedure in the current step in a state where the content is rewound to the start point of the current step, and the measurement unit 12 may reset the working time count of the current step to zero. For example, when an input to pause is entered during the display of content in the third step of the manual cleaning step (in a narrow sense), the display control unit 11 puts the display of the content back to the beginning of the third step (at the time when 0 seconds have elapsed), and the measurement unit 12 changes the working time count of the third step to 0 seconds.

As described, when an input to pause is entered, the display of the content and the working time count are put back to the respective initial values in the current step, thereby the cleaner can start over the work from the beginning of the current step at the time of resuming the work. For example, when the cleaner has left the cleaning work for a long period of time, the cleaner often forgets the progress status of the work of the current step. In this case, starting over the work from the beginning of the current step can reduce the risk of resulting in insufficient work in the current step.

The above example is an example of a case where the cleaner enters an input to pause when the cleaner suspends the cleaning work. In the following, an example will be described of a case where the cleaner does not enter an input to pause when the cleaner suspends the cleaning work. When the cleaner does not enter an input to pause even when the cleaning work is suspended, the control unit 10 recognizes through the following method that the cleaning work is suspended.

When the operation reception unit 50 has not received an update instruction input for proceeding to the subsequent step for a certain period of time (for example, 30 seconds) after the reference period of time has elapsed or after the reproduction of the moving image of the content has ended in the current step, it is determined that the current step has not been performed.

More specifically, the measurement unit 12 continues counting the measures period of time even after the measured period of time reaches the reference period of time of the current step. The comparison determination unit 13 compares the measured period of time measured by the measurement unit 12 with a total time obtained by adding the above certain period of time to the reference period of time or the content reproduction time of the current step. When the operation reception unit 50 has not received the update instruction input before the measured period of time exceeds the total time, the display control unit 11 displays information prompting the cleaner to start over the current step on the screen.

Alternatively, after the measured period of time reaches the reference period of time of the current step, the measurement unit 12 newly starts counting the excess time. The comparison determination unit 13 compares the excess time measured by the measurement unit 12 with the certain period of time. When the operation reception unit 50 has not received the update instruction input before the excess time exceeds the certain period of time, the display control unit 11 displays information prompting the cleaner to start over the current step on the screen. The display control unit 11 may simply display a message such as "Update operation has not been entered" on the screen.

For example, the display control unit 11 displays on the screen a confirmation message for selecting whether or not to start over the current step. When the cleaner enters an input selecting to start over to the operation input device 3 or the operation unit 32 and the operation reception unit 50 receives the input, the display control unit 11 rewinds the content displaying the procedure in the current step to the start point of the current step, and the measurement unit 12 resets the working time (measured period of time) count of the current step to zero. When the cleaner does not enter an input selecting to start over to the operation input device 3 or the operation unit 32, the display control unit 11 continues to display the content in the current step, and the measurement unit 12 continues to count the working time (measured period of time) of the current step.

When the cleaner does not enter an input to pause even when the cleaning work is suspended, the control unit 10 determines whether or not the cleaning work is suspended based on an image captured by the image-capturing unit 40. In this example, the installation position of the endoscope cleaning work support device 1 needs to be fixed. For example, the endoscope cleaning work support device 1 is installed at a position facing the cleaner across the cleaning table.

The image-capturing unit 40 captures a plurality of images, per person, of the face of the cleaner cleaning an endoscope in advance. An image recognition unit (not shown) in the control unit 10 generates a face identifier for each cleaner based on the plurality of captured images. When the endoscope cleaning work support device 1 is installed at a position facing the cleaner, a front face identifier is generated. When the endoscope cleaning work support device 1 is installed on the side of the cleaning table, a side face identifier is generated. A face identifier of a general face may be used instead of a face identifier of a specific cleaner. In this case, it is not possible to tell which cleaner is cleaning.

The image-capturing unit 40 continues image capturing while the content is displayed by the display control unit 11. The image recognition unit detects the face of the cleaner from images captured by the image-capturing unit 40 using the face identifiers. The control unit 10 determines that the cleaning work is suspended when the face of the cleaner has not faced the display unit 31 for a certain period of time (for example, 30 seconds).

More specifically, the measurement unit 12 measures a non-detection period of time during which the face of the cleaner is not facing the display unit 31 based on the captured images while the display control unit 11 is displaying the content. More specifically, the measurement unit 12 measures a period of time from when the face can no longer be detected by the face identifier to when the face can be detected again by the face identifier in the captured images. The comparison determination unit 13 compares the non-detection period of time measured by the measurement unit 12 with the certain period of time. When the non-detection period of time is equal to or more than the certain period of time, the display control unit 11 displays information prompting the cleaner to start over the current step on the screen.

For example, the display control unit 11 displays on the screen a confirmation message for selecting whether or not to start over the current step. When the cleaner enters an input selecting to start over to the operation input device 3 or the operation unit 32 and the operation reception unit 50 receives the input, the display control unit 11 rewinds the content displaying the procedure in the current step to a point in time when it is detected that the face of the cleaner is not facing the display unit 31, and the measurement unit 12 puts back the working time count of the current step to a point in time when it is detected that the face of the cleaner is not facing the display unit 31. When the cleaner does not enter an input selecting to start over to the operation input device 3 or the operation unit 32, the display control unit 11 continues to display the content in the current step, and the measurement unit 12 continues to count the working time of the current step.

A human-detecting sensor may be used instead of the image-capturing unit 40 to determine whether or not the cleaning work is suspended. In this example, the endoscope cleaning work support device 1 needs to include a human-detecting sensor (not shown). The human-detecting sensor detects the presence or absence of a person within a predetermined range from the display unit 31 and outputs the result to the control unit 10. The control unit 10 determines that the cleaning work is suspended when no person exists within the predetermined range from the display unit 31 for a certain period of time (for example, 30 seconds).

More specifically, the measurement unit 12 measures a non-detection period of time during which no person is present within the predetermined range from the display unit 31 while the display control unit 11 is displaying the content. More specifically, based on the detection result from the human-detecting sensor, the measurement unit 12 measures a period of time from when a person is no longer present to when a person is present again within the predetermined range from the display unit 31. The comparison determination unit 13 compares the non-detection period of time measured by the measurement unit 12 with the certain period of time. When the non-detection period of time is equal to or more than the certain period of time, the display control unit 11 displays information prompting the cleaner to start over the current step on the screen.

For example, the display control unit 11 displays on the screen a confirmation message for selecting whether or not to start over the current step. When the cleaner enters an input selecting to start over to the operation input device 3 or the operation unit 32 and the operation reception unit 50 receives the input, the display control unit 11 rewinds the content displaying the procedure in the current step to a point in time when it is detected that a person is no longer present within the predetermined range, and the measurement unit 12 puts back the working time count of the current step to a point in time when it is detected that a person is no longer present within the predetermined range. When the cleaner does not enter an input selecting to start over to the operation input device 3 or the operation unit 32, the display control unit 11 continues to display the content in the current step, and the measurement unit 12 continues to count the working time of the current step.

As described above, according to the second exemplary embodiment, even when work that is interrupting emerges such as helping other staff and the cleaning work is temporarily suspended, by restarting the reproduction of the content from the beginning of the suspended step or from where the step is suspended, the cleaner can accurately perform the manual cleaning step (in a broad sense) according to the guide display. By restarting the counting of the working time from the beginning of the suspended step or from where the step is suspended, the accurate working time of each step can be recorded.

Third Exemplary Embodiment

In the third exemplary embodiment, a step is provided in which an update instruction input from the cleaner is not received until a predetermined period of time necessary for ending the step has elapsed after the content is started being displayed by the display control unit 11. With regard to a specific step included in the manual cleaning step (in a broad sense), the comparison determination unit 13 compares a predetermined period of time required for ending the step with a measured period of time measured by the measurement unit 12. Even when the operation reception unit 50 receives an input for displaying a procedure for a step subsequent to the current step, the display control unit 11 performs control such that the content in the subsequent step is not displayed until the measured period of time exceeds the predetermined period of time.

A critical step with high importance is designated as the specific step. For example, a leak test step is designated as the specific step. In the leak test step for checking whether or not a hole is formed in an endoscope, the endoscope is immersed in water for 30 seconds and then checked for whether or not air bubbles are continuously generated from the endoscope. When the display control unit 11 starts displaying content in the leak test step, the display control unit 11 starts a countdown of 30 seconds. The control unit 10 invalidates an update instruction input from a cleaner until the countdown ends.

Figure 8:
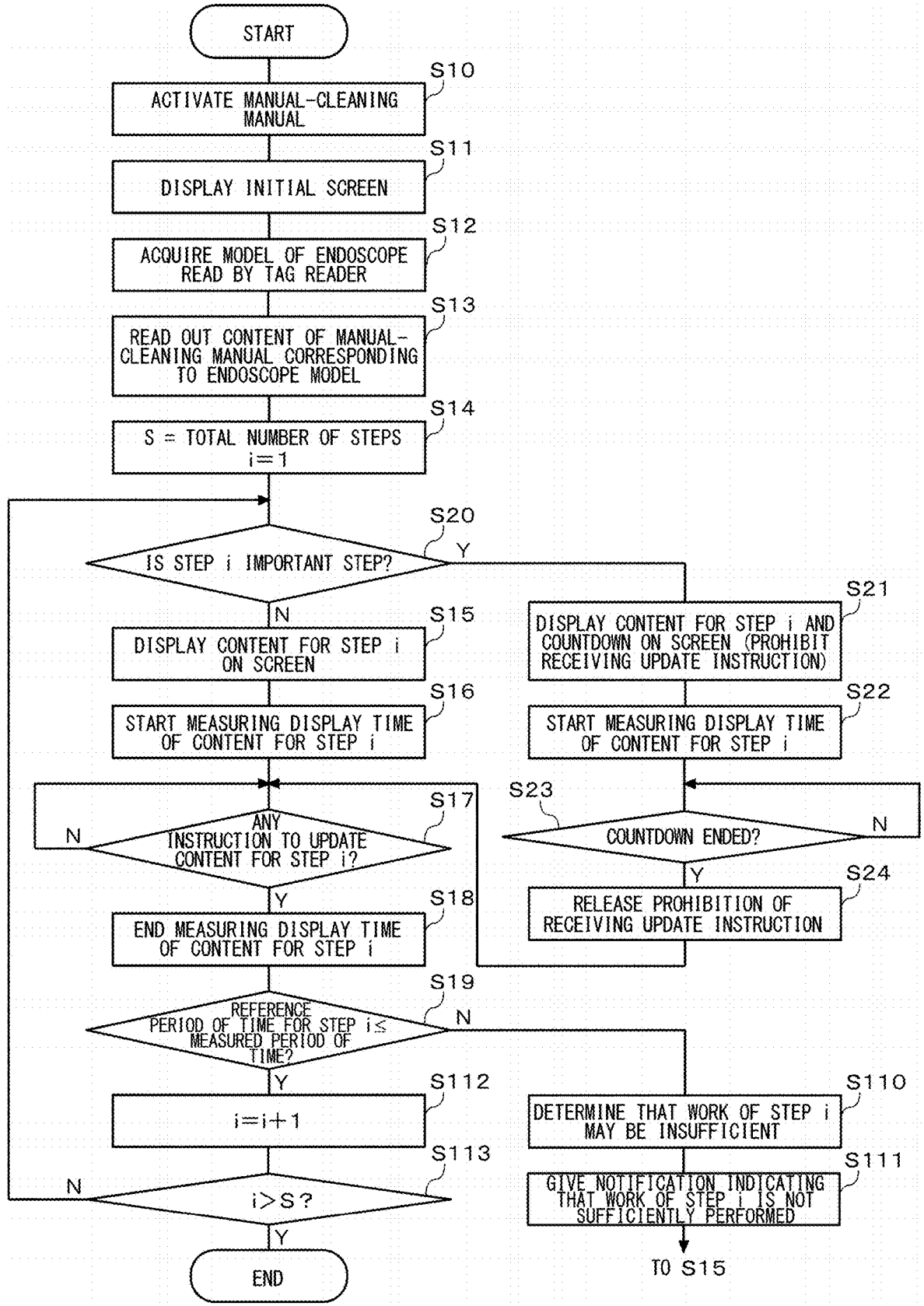
FIG. 8 is a flowchart illustrating a flow of a cleaning work support process according to the third exemplary embodiment.

FIG. 8 is a flowchart illustrating a flow of a cleaning work support process according to the third exemplary embodiment. The flowchart according to the third exemplary embodiment illustrated in FIG. 8 is obtained by adding the processes of steps S21 to S24 to the flowchart according to the first exemplary embodiment illustrated in FIG. 5. Hereinafter, an explanation will be given regarding the processes that are added, and the description of the processes that are the same as those in FIG. 5 will be appropriately omitted. The control unit 10 reads the cleaning manual content from the cleaning manual content storage 21 (S13), sets the total number of steps of the read cleaning manual content as a parameter S, and sets 1 as the initial value for a parameter i (S14).

The control unit 10 determines whether or not a step i is an important step. When the step i is not an important step (N in S20), the same processes as the processes in step S15 and the following steps that are shown in FIG. 5 are performed. When the step i is an important step (Y in S20), the display control unit 11 displays the content in the step i and the specified countdown in the step i on the screen of the display unit 31 (S25). At the same time as the start of the display, the control unit 10 prohibits receiving an update instruction input from a cleaner.

The measurement unit 12 starts measuring the display time of the content for the step i (S22). The comparison determination unit 13 determines whether or not the countdown has been ended (S23). When the countdown is ended (Y in S23), the control unit 10 releases the prohibition of receiving an update instruction input from a cleaner (S24). The step proceeds to step S17 so as to wait for an instruction to update the content in the step i to be entered by the cleaner. Other processes are the same as those in the flowchart shown in FIG. 5.

Figure 9:
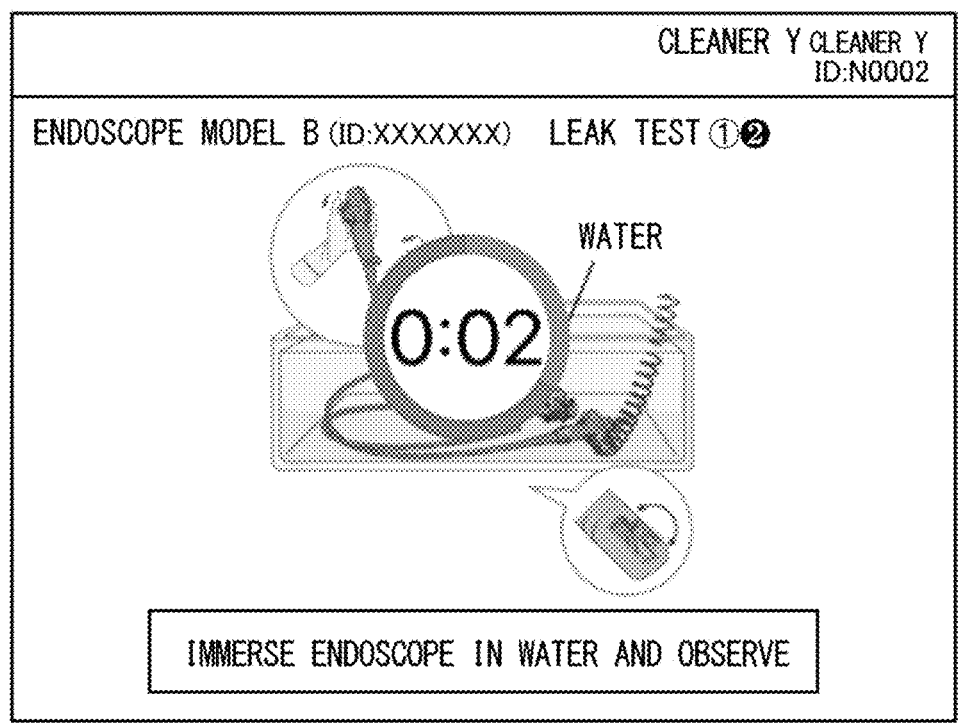
FIG. 9 is a diagram showing an example of content in the first step of a leak test step.

FIG. 9 is a diagram showing an example of content in the first step of the leak test step. A leak test step for an endoscope model B shown in FIG. 9 includes two minor steps. FIG. 9 shows content for a step of immersing the endoscope in water and observing whether or not bubbles are generated, which is the first step of the leak test step. On this screen, in addition to an object indicating the work details of the step, an object for count down from a specified value (for example, 30 seconds) to 0 seconds is displayed in a superimposed manner. Until the time object reaches 0 seconds, an update instruction input from the cleaner cannot be received.

As described above, according to the third exemplary embodiment, the cleaner can be prompted to perform more secure work for an important step by prohibiting the entry of an update instruction input from the cleaner for a specified period of time after the display of the content is started for the important step.

Fourth Exemplary Embodiment

In the fourth exemplary embodiment, cleaning manual content that displays more detailed procedure is selected as a period of time during which the cleaner does not clean the endoscope becomes longer. The display control unit 11 controls the manual content to be displayed on the screen. For example, when the cleaner has not cleaned an endoscope of the target model for a period of time that is longer than the reference period of time, cleaning manual content of a skill level that is lower than that of the cleaner for the model is displayed.

Figure 10:
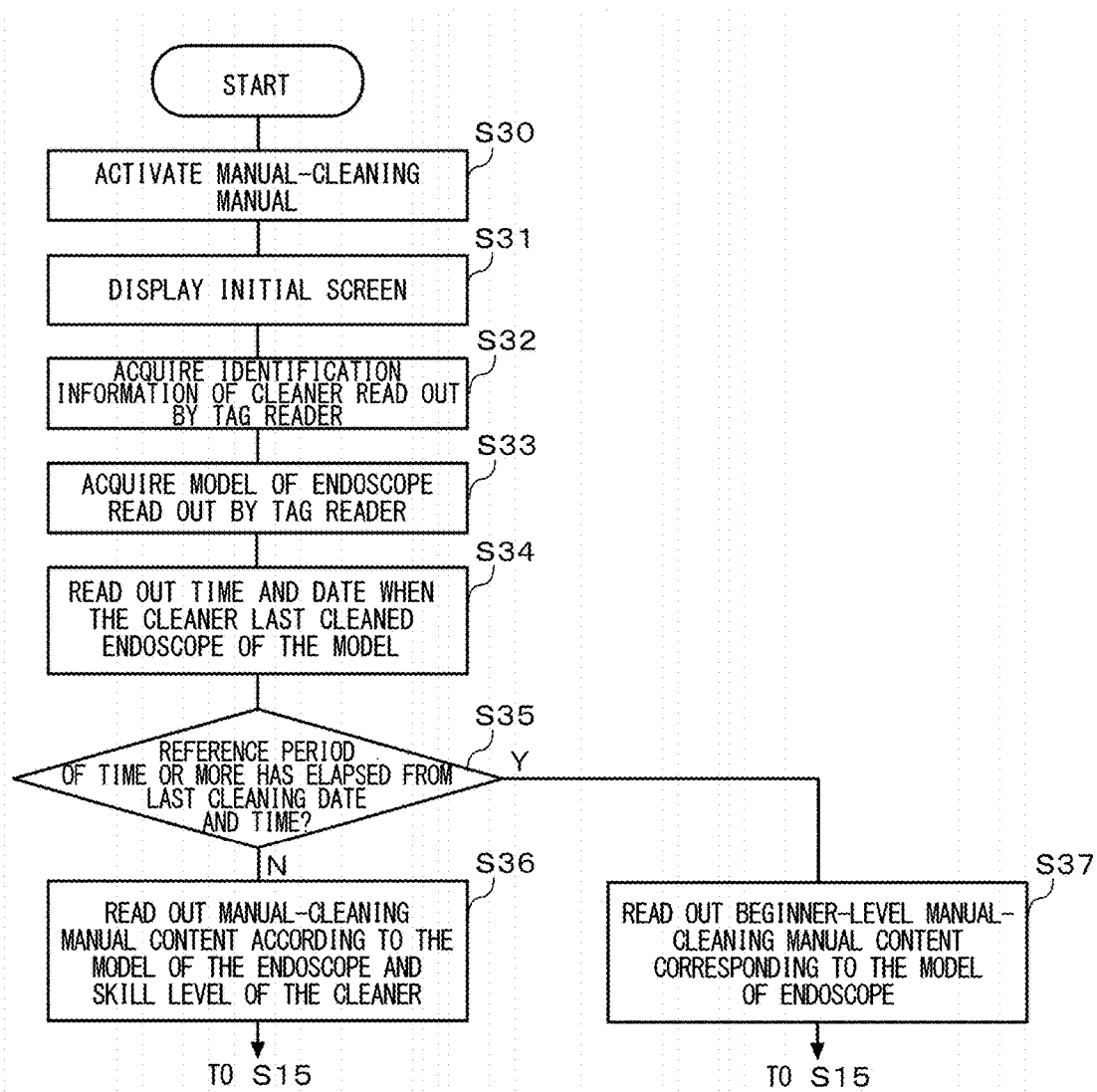
FIG. 10 is a flowchart illustrating an example of a flow of a cleaning work support process according to the fourth exemplary embodiment.

FIG. 10 is a flowchart illustrating an example of a flow of a cleaning work support process according to the fourth exemplary embodiment. The control unit 10 of the endoscope cleaning work support device 1 activates a manual-cleaning manual application (S30) and displays the initial screen of the manual-cleaning manual application on the display unit 31 (S31). The control unit 10 acquires the identification information of the cleaner included in cleaner information read by the tag reader 2 (S32). The control unit 10 acquires the model of an endoscope included in endoscope information read by the tag reader 2 (S33).

The control unit 10 refers to the manual cleaning history storage 22 based on the identification information of the cleaner and the model of the endoscope that have been acquired and reads out the date and time when the cleaner last cleaned an endoscope of the model (S34). The control unit 10 determines whether or not the reference period of time (for example, half a year) has elapsed from the date and time that is read (S35). When the reference period of time has not elapsed (N in S35), the control unit 10 reads out cleaning manual content according to the model of the endoscope and the skill level of the cleaner (S36). Hereinafter, processes in step S15 and the following steps in FIG. 5 are performed.

When the reference period of time has elapsed (Y in S35), the control unit 10 reads out beginner-level cleaning manual content corresponding to the model of the endoscope (S37). Hereinafter, processes in step S15 and the following steps in FIG. 5 are performed.

According to the fourth exemplary embodiment, as described above, when cleaning an endoscope of a model for which a long period of time has passed since the last cleaning, content showing a more detailed procedure is displayed. Thereby, it is possible to prevent an error from occurring during the cleaning work due to the memory being vague.

Fifth Exemplary Embodiment

Figure 11:
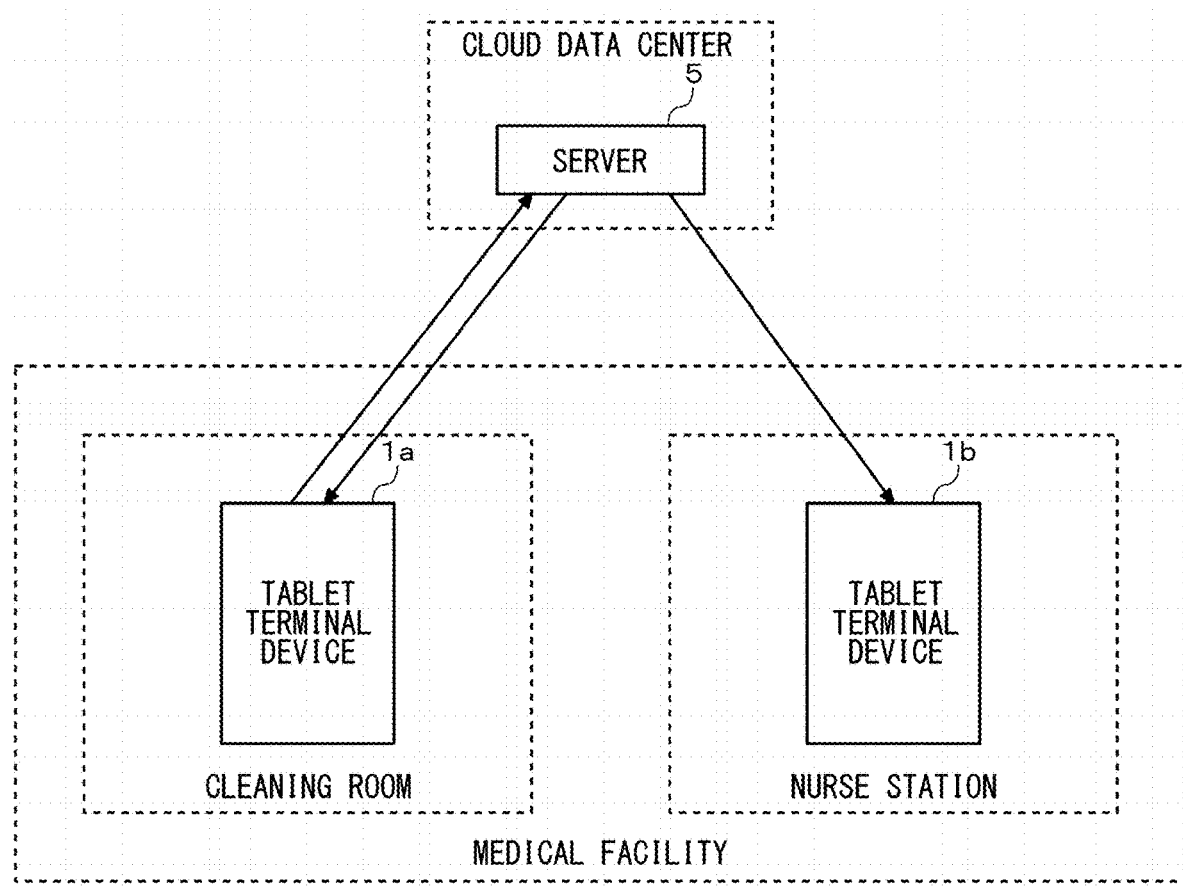
FIG. 11 is a block diagram showing the overall configuration of the fifth exemplary embodiment.

FIG. 11 is a block diagram showing the overall configuration of the fifth exemplary embodiment. In the fifth exemplary embodiment, the supervisor in charge of the cleaner keeps a tablet terminal device 1b similar to a tablet terminal device 1a installed in the cleaning room. The supervisor usually stays in a nurse station. Each of the tablet terminal devices 1a and 1b can wirelessly access a server 5 installed in a cloud data center. With this configuration, cleaning history information of an endoscope can be recorded in a recording device of the server 5. The server 5 may be a server installed in a medical facility.

When the tablet terminal device 1a installed in the cleaning room determines that the working time of a certain step is insufficient, the tablet terminal device 1a displays alert information on the own display unit 31 and transmits the alert information to the server 5. Upon receiving the alert information from the tablet terminal device 1a installed in the cleaning room, the server 5 transfers the alert information to the tablet terminal device 1b kept by the supervisor. The alert information includes the name of the cleaner.

Upon receiving the alert information, the tablet terminal device 1b kept by the supervisor displays the alert information including the name of the cleaner on the own display unit 31. The supervisor looking at the screen of the display unit 31 can identify the corresponding cleaner based on the displayed details and immediately give guidance.

According to the fifth exemplary embodiment, when the cleaner performs insufficient work in manual cleaning, the cleaner can immediately receive guidance from the supervisor. As a result, the skill of the cleaner can be improved, and the risk of an insufficient cleaning work being overlooked can be reduced. The exemplary embodiment 5 is particularly effective in a large-scale medical facility where a plurality of cleaning tables are installed.

Described above is an explanation on the present invention based on the exemplary embodiments. These exemplary embodiments are intended to be illustrative only, and it will be obvious to those skilled in the art that various modifications to constituting elements and processes could be developed and that such modifications are also within the scope of the present invention.

In the above embodiments, examples in which a tablet terminal device is used as the endoscope cleaning work support device 1 has been described. In this regard, a smartphone terminal, a Phablet terminal, a wearable terminal, a notebook PC, or a desktop PC may be used instead of the tablet terminal device. When a desktop PC is used, the display unit 31, the operation input device 3, and the tag reader 2 are installed near a cleaning stand, and the main body may be installed at a remote place.

What is claimed is:

1. An endoscope cleaning work support device comprising:
   a memory for storing a step-by-step procedure for manual cleaning of an endoscope;
   a display; and
   a processor comprising hardware, wherein the processor is configured to:
      retrieve the step-by step procedure for manual cleaning of the endoscope from the memory;
      receive input from a user;
      control a display so as to display the step-by-step procedure for manual cleaning of the endoscope;
      measure a first period of time from a start time of a procedure in a current step marked by reception of a first input from the user for displaying the procedure in the current step, to an end time of the procedure in the current step marked by reception of a second input from the user for displaying a procedure in a subsequent step; and
      display on the display, information for alerting the user that the user's performance of the current step for manual cleaning of the endoscope may be insufficient, when the first period of time exceeds a period of time derived from adding a reference period of time defined for each step for displaying the procedure and a predetermined period of time, and when an input is not received for displaying a procedure in a step subsequent to the current step.

2. The endoscope cleaning work support device according to claim 1, wherein the processor is further configured to determine that work of the current step has not been done sufficiently when the first period of time is shorter than the reference period of time.

3. The endoscope cleaning work support device according to claim 1, wherein the processor is further configured to:
measure a second period of time elapsed after the display of the procedure is ended;
compare the predetermined period of time with the second period of time; and
display on the display, information for alerting the cleaner, when the second period of time exceeds the predetermined period of time, and when an input is not received for displaying a procedure in a step subsequent to the current step.

4. The endoscope cleaning work support device according to claim 1, further comprising:
a first detector for capturing images of the face of the cleaner,
wherein the processor is configured to:
measure a third period of time during which the direction of the face of the cleaner does not face the direction of the display while displaying the procedure;
compare the predetermined period of time with the third period of time; and
display on the display, information for alerting the cleaner when the third period of time is the predetermined period of time or longer.

5. The endoscope cleaning work support device according to claim 1, further comprising:
a second detector that detects the presence or absence of a person within a predetermined range from the display,
wherein the processor is configured to:
measure a fourth period of time during which the person does not exist within the predetermined range while displaying the procedure;
compare the predetermined period of time with the fourth period of time; and
display on the display, information for alerting the cleaner when the fourth period of time is the predetermined period of time or longer.

6. The endoscope cleaning work support device according to claim 1, wherein the processor is further configured to:
with regard to a specific step in a plurality of steps for manually cleaning an endoscope, compare a predetermined period of time required for ending the step with the first period of time; and
even when an input is received for displaying a procedure for a step subsequent to the current step, control such that a procedure in the subsequent step is not displayed until the first period of time exceeds the predetermined period of time.

7. The endoscope cleaning work support device according to claim 1, wherein the processor is configured to control the display such that a still image or a moving image is displayed as the procedure.

8. The endoscope cleaning work support device according to claim 1, wherein the processor is configured to control the display such that a procedure according to the type of the endoscope is displayed.

9. The endoscope cleaning work support device according to claim 1, wherein the processor is configured to control the display such that a procedure according to the skill level of the cleaner for cleaning an endoscope.

10. The endoscope cleaning work support device according to claim 1, wherein the processor is configured to control the display such that a more detailed procedure is displayed as a period of time during which the cleaner does not clean the endoscope becomes longer.

11. The endoscope cleaning work support device according to claim 1, wherein the processor is configured to rewind the procedure for a predetermined period of time or control such that the procedure is rewound to a start point when an input is received for pausing the display of the procedure.

12. The endoscope cleaning work support device according to claim 1, further comprising:
a first sensor for detecting an endoscope type being cleaned from a plurality of endoscope types stored in the memory;
wherein the memory stores the step-by-step procedure for manual cleaning of the plurality of endoscopes, each being a different endoscope type;
wherein the processor is configured to:
receive input from the first sensor identifying the endoscope type being cleaned; and
based on the received input, retrieve the step-by step procedure for manual cleaning of the endoscope type being cleaned from the memory.

13. A method of operating an endoscope cleaning work support device, the method comprising:
storing a step-by-step procedure for manual cleaning of an endoscope;
retrieving the step-by step procedure for manual cleaning of the endoscope from the memory;
receiving input from a user;
controlling a display so as to display the step-by-step procedure for manual cleaning of the endoscope;
measuring a first period of time from a start time of a procedure in a current step marked by reception of a first input from the user for displaying the procedure in the current step, to an end time of the procedure in the current step marked by reception of a second input from the user for displaying a procedure in a subsequent step; and
displaying on the display, information for alerting the user that the user's performance of the current step for manual cleaning of the endoscope being cleaned may be insufficient, when the first period of time exceeds a period of time derived from adding a reference period of time defined for each step for displaying the procedure and a predetermined period of time, and when an input is not received for displaying a procedure in a step subsequent to the current step.

14. The method of operating an endoscope cleaning work support device according to claim 13, further comprising:
measuring a second period of time elapsed after the display of the procedure is ended;
comparing the predetermined period of time with the second period of time; and
displaying on the display, information for alerting the cleaner, when the second period of time exceeds the predetermined period of time, and when an input is not received for displaying a procedure in a step subsequent to the current step.

15. The method of operating an endoscope cleaning work support device according to claim 13, further comprising:
with regard to a specific step in a plurality of steps for manually cleaning an endoscope, comparing a predetermined period of time required for ending the step with the first period of time; and
even when an input is received for displaying a procedure for a step subsequent to the current step, control such that a procedure in the subsequent step is not displayed until the first period of time exceeds the predetermined period of time.

16. The method of operating an endoscope cleaning work support device according to claim 13, further comprising:
detecting an endoscope type being cleaned from a plurality of endoscope types stored in the memory, wherein the memory stores the step-by-step procedure for manual cleaning of the plurality of endoscopes, each being a different endoscope type;
receiving an input from the first sensor identifying the endoscope type being cleaned; and
based on the received input, retrieving the step-by step procedure for manual cleaning of the endoscope type being cleaned from the memory.

17. An endoscopic cleaning work support program embedded in a computer readable recording medium, comprising:
a module that retrieves a step-by step procedure for manual cleaning of an endoscope from a memory;
a module that receives input from a user;
a module that controls a display so as to display the step-by-step procedure for manual cleaning of the endoscope;
a module that measures a first period of time from a start time of a procedure in a current step marked by reception of a first input from the user for displaying the procedure in the current step, to an end time of the procedure in the current step marked by reception of a second input from the user for displaying a procedure in a subsequent step; and
a module that displays on the display, information for alerting the user that the user's performance of the current step for manual cleaning of the endoscope being cleaned may be insufficient, when the first period of time exceeds a period of time derived from adding a reference period of time defined for each step for displaying the procedure and a predetermined period of time, and when an input is not received for displaying a procedure in a step subsequent to the current step.

18. The endoscope cleaning work support program according to claim 17, further comprising:
a module that measures a second period of time elapsed after the display of the procedure is ended;
a module that compares the predetermined period of time with the second period of time; and
a module that displays on the display, information for alerting the cleaner, when the second period of time exceeds the predetermined period of time, and when an input is not received for displaying a procedure in a step subsequent to the current step.

19. The endoscope cleaning work support program according to claim 17, further comprising:
a module that compares, with regard to a specific step in a plurality of steps for manually cleaning an endoscope, a predetermined period of time required for ending the step with the first period of time; and
a module that, even when an input for displaying a procedure for a step subsequent to the current step is received, controls such that a procedure in the subsequent step is not displayed until the first period of time exceeds the predetermined period of time.

20. The endoscopic cleaning work support program according to claim 17, further comprising:
a module for detecting an endoscope type being cleaned from a plurality of endoscope types stored in the memory, wherein the memory stores the step-by-step procedure for manual cleaning of the plurality of endoscopes, each being a different endoscope type;
a module for receiving an input from the first sensor identifying the endoscope type being cleaned; and
a module for, based on the received input, retrieving the step-by step procedure for manual cleaning of the endoscope type being cleaned from the memory.

* * * * *